United States Patent
Hammill, Sr. et al.

(10) Patent No.: US 12,245,796 B1
(45) Date of Patent: Mar. 11, 2025

(54) SPINAL FIXATION SYSTEM HAVING A LOCKABLE CONNECTOR

(71) Applicant: Complex Spinal, LLC, Palm Beach Gardens, FL (US)

(72) Inventors: John E. Hammill, Sr., Palm Beach Gardens, FL (US); Greg Lentner, Palm Beach Gardens, FL (US)

(73) Assignee: Complex Spinal, LLC, Palm Beach Gardens, FL (US)

(*) Notice: Subject to any disclaimer, the term of this patent is extended or adjusted under 35 U.S.C. 154(b) by 0 days.

(21) Appl. No.: 18/663,796

(22) Filed: May 14, 2024

(51) Int. Cl.
*A61B 17/70* (2006.01)

(52) U.S. Cl.
CPC ...... *A61B 17/7035* (2013.01); *A61B 17/7002* (2013.01); *A61B 17/7032* (2013.01)

(58) Field of Classification Search
CPC .................................. A61B 17/7032–17/7037
See application file for complete search history.

(56) References Cited

U.S. PATENT DOCUMENTS

| | | | |
|---|---|---|---|
| 255,428 | A | 3/1882 | Graham |
| 590,204 | A | 9/1897 | Archer |
| 4,378,187 | A | 3/1983 | Fullerton |
| 4,419,026 | A | 12/1983 | Leto |
| 4,836,196 | A | 6/1989 | Park et al. |
| 4,854,304 | A | 8/1989 | Zielke |
| 4,887,595 | A | 12/1989 | Heinig et al. |
| 4,887,596 | A | 12/1989 | Sherman |
| 4,946,458 | A | 8/1990 | Harms et al. |
| 4,950,269 | A | 8/1990 | Gaines, Jr. |
| 5,002,542 | A | 3/1991 | Frigg |
| 5,110,244 | A | 5/1992 | Garman |
| 5,129,900 | A | 7/1992 | Asher et al. |
| 5,133,717 | A | 7/1992 | Chopin |
| 5,324,150 | A | 6/1994 | Fullerton |
| 5,427,488 | A | 6/1995 | Fullerton et al. |
| 5,443,467 | A | 8/1995 | Biedermann et al. |

(Continued)

FOREIGN PATENT DOCUMENTS

| | | |
|---|---|---|
| EP | 0836835 A2 | 4/1998 |
| EP | 0836835 A3 | 4/1998 |

(Continued)

OTHER PUBLICATIONS

Anonymous, "Versalok Low Back Fixation System—Instrumentation Manual", Wright Medical Technology, Inc.—Arlington, TN, pp. 1-10, (1997).

(Continued)

*Primary Examiner* — Julianna N Harvey
(74) *Attorney, Agent, or Firm* — McHale & Slavin, P.A.

(57) ABSTRACT

A spinal fixation system for use in securing a spinal rod to a vertebra using a lockable bone screw connector. The connector is configured to be movably connected to the head of a bone screw, and a spinal rod can then be used to physically connect a first vertebra to a second vertebra. The spinal fixation system includes a tool grasping the connector by a locking and/or unlocking instrument that can allow the connector to lock to the bone screw by moving a collet, while the connector can still move along the spinal rod until locked into place by a set screw. The connector can be selectively unlocked from the bone screw for adjustment or removal.

11 Claims, 5 Drawing Sheets

(56) References Cited

U.S. PATENT DOCUMENTS

| | | |
|---|---|---|
| 5,487,744 A | 1/1996 | Howland |
| 5,549,608 A | 8/1996 | Errico et al. |
| 5,569,247 A | 10/1996 | Morrison |
| 5,584,834 A | 12/1996 | Errico et al. |
| 5,591,166 A | 1/1997 | Bernhardt et al. |
| 5,613,816 A | 3/1997 | Cabahug |
| 5,628,740 A | 5/1997 | Mullane |
| 5,669,911 A | 9/1997 | Errico et al. |
| 5,683,392 A | 11/1997 | Richelsoph et al. |
| 5,716,357 A | 2/1998 | Rogozinski |
| 5,733,285 A | 3/1998 | Errico et al. |
| 5,749,690 A | 5/1998 | Kutz |
| 5,788,443 A | 8/1998 | Cabahug |
| 5,800,435 A | 9/1998 | Errico et al. |
| 5,863,293 A | 1/1999 | Richelsoph |
| 5,947,966 A | 9/1999 | Drewry et al. |
| 5,964,760 A | 10/1999 | Richelsoph |
| 5,997,539 A | 12/1999 | Errico et al. |
| 6,010,503 A | 1/2000 | Richelsoph |
| 6,050,997 A | 4/2000 | Mullane |
| 6,063,090 A | 5/2000 | Schlapfer |
| 6,090,111 A | 7/2000 | Nichols |
| 6,102,952 A | 8/2000 | Koshino |
| 6,113,600 A | 9/2000 | Drummond et al. |
| 6,132,432 A | 10/2000 | Richelsoph |
| 6,162,234 A | 12/2000 | Freedland et al. |
| 6,187,005 B1 | 2/2001 | Brace et al. |
| RE37,227 E | 6/2001 | Brodbeck |
| 6,254,602 B1 | 7/2001 | Justis |
| 6,273,888 B1 | 8/2001 | Justis |
| 6,355,040 B1 | 3/2002 | Richelsoph et al. |
| RE37,665 E | 4/2002 | Ralph et al. |
| 6,413,258 B1 | 7/2002 | Bernhardt, Jr. |
| 6,416,515 B1 | 7/2002 | Wagner |
| 6,454,773 B1 | 9/2002 | Sherman et al. |
| 6,478,798 B1 | 11/2002 | Howland |
| 6,565,565 B1 | 5/2003 | Yuan et al. |
| 6,595,992 B1 | 7/2003 | Wagner et al. |
| 6,602,255 B1 | 8/2003 | Campbell et al. |
| 6,610,062 B2 | 8/2003 | Bailey et al. |
| 6,610,063 B2 | 8/2003 | Kumar et al. |
| 6,623,485 B2 | 9/2003 | Doubler et al. |
| 6,626,906 B1 | 9/2003 | Young |
| 7,105,029 B2 | 9/2006 | Doubler et al. |
| 7,335,201 B2 | 2/2008 | Doubler et al. |
| 7,658,582 B2 | 2/2010 | Doubler et al. |
| 7,744,633 B2 | 6/2010 | Berrevoets et al. |
| RE42,867 E | 10/2011 | Hammill, Sr. et al. |
| 9,649,135 B2 | 5/2017 | Doubler et al. |
| 10,136,925 B2 | 11/2018 | Shoshtaev |
| 10,507,043 B1 * | 12/2019 | Gladieux ............ A61B 17/8605 |
| 10,751,090 B2 | 8/2020 | Biedermann et al. |
| 2002/0114680 A1 | 8/2002 | Stoewer et al. |
| 2003/0149487 A1 | 8/2003 | Doubler et al. |
| 2004/0162560 A1 * | 8/2004 | Raynor .................. F16B 33/02 403/362 |
| 2005/0053423 A1 | 3/2005 | Doubler et al. |
| 2007/0286703 A1 | 12/2007 | Doubler et al. |
| 2010/0114180 A1 * | 5/2010 | Rock .................. A61B 17/7037 606/308 |
| 2013/0060293 A1 * | 3/2013 | Jackson ............. A61B 17/7037 606/305 |
| 2019/0150989 A1 * | 5/2019 | Biester ............... A61B 17/7001 |

FOREIGN PATENT DOCUMENTS

| | | |
|---|---|---|
| EP | 0947174 A3 | 10/1999 |
| EP | 0947174 B1 | 10/1999 |

OTHER PUBLICATIONS

Anonymous, ", Strong, Simple and Low Profile—Ovation Polyaxial System", Osteotech, Inc. Spinal Systems.—Eatontown, NJ, pp. 1-6, (1999).

* cited by examiner

SPINAL FIXATION SYSTEM HAVING A LOCKABLE CONNECTOR

FIELD OF THE INVENTION

The instant invention relates to field of orthopedic surgery, namely a spinal fixation system for use in securing a spinal rod to a vertebra using a lockable bone screw connector.

BACKGROUND OF THE INVENTION

Spinal rod systems for use in facilitating spinal fusion, and for correcting and stabilizing spinal curvatures to correct spinal disorders or degenerative conditions, are well known in the art. Spinal rod systems include two or more bone screws with connector members coupled together with spinal rods. The conventional bone screw has a proximal end constructed and arranged to secure to a vertebrae, and a connector coupled to the distal end of the bone screw for receipt of a spinal rod. During a spinal correction procedure, a plurality of bone screws with connector members are fixed to vertebrae at various points on each side of the spinal midline. Thereafter, each of the connector members are on each side of the spinal midline and linked with the other fixation members by an elongated spinal rod, such that the spinal rod extends vertically along at least a portion of the length of the spine.

It is common practice to place bone screws into the vertebral bodies and then connect a metal rod between the bone screws to create a rigid structure between adjacent vertebral bodies. The spinal rod connector members are used for transversely and rigidly connecting adjacent spinal members together. By providing a rigid transverse connection between adjacent spinal rods, a stiffer construct can be created to enhance the promotion of spinal fusion.

Spinal rods are mounted by a surgeon in a custom-fit manner, both in length and angular positioning. Bending of the rod is common so that the rod is holding the vertebral portions in proper relation. There is not a predetermined distance between two spinal rods, and the rods may converge or diverge from each other. One spinal rod may have a portion directed at an angle different from that of a second other rod.

For these reasons there remains a need for a device which, in one simple action such as squeezing a lever, can reduce a posteriorly introduced rod into a pedicle screw and securely lock the connector to the pedicle screw to allow placement of the rod. Conversely, there remains a need for a similar device which, through an equally simple action, can unlock the connector from a pedicle screw thereby releasing the connector and adjoining rod from a set position.

Known prior art includes: U.S. Pat. No. 5,947,966 discloses a transverse connector system for linking adjacent spinal rods together. The system includes first and second connector portions which are slidably adjustable in relation to each other. Each connector portion includes an engaging member configured to receive a spinal rod. A wedge member is provided in each engaging member to secure each connector portion to the spinal rod. The wedge member includes a screw for engaging and biasing the spinal rod into a receptacle defined by the engaging member.

U.S. Pat. No. 5,683,392 discloses a multi planar locking mechanism for securing a spinal rod to the spinal column. The locking mechanism includes a bone fixation member for attachment to the bone member, the bone fixation member having a spherical portion; an inner housing member having a channel for receiving the rod and having a spherical portion for engaging the spherical portion of the bone fixation member; and an outer housing member for locking the inner housing member to the rod and the spherical portion of the bone fixation member.

U.S. Pat. No. 6,413,258 discloses a rod-to-rod coupler which includes a body having first and second coupler portions. Each coupler portion defines a concavity configured to receive a portion of an elongated spinal rod. A screw and nut assembly, which includes a screw and a flanged nut, is positioned adjacent each concavity. Each flanged nut has a flange portion which extends at least partially over one concavity.

U.S. Pat. No. 6,113,600 discloses a spinal fixation system having a pair of longitudinal members positionable adjacent the spine, an engaging member for engaging longitudinal members to the spine, a pair of wedge members each having a bearing surface configured to bear on a longitudinal member, and a connector configured to span a distance between the longitudinal members. The connector includes a pair of engaging members each having a fixation surface and a connecting surface, and a bridge member attached to the connecting surfaces.

U.S. Pat. No. 7,744,633 discloses a crosslink member for securing spinal rods having connector ends that include a brace and a locking member, each connector include an arcuate face resting on and securing a spinal rod. The locking member is a cam member that rotates relative to the locking member and engages the connector to displace the cam member. The crosslink includes a male connector with a cylindrical cross rod received by a cavity in a female connector. The cross rod is secured by a pivotable clamp device in the female connector, and the cross rod connector and female connector may pivot, rotate, and telescope relative to each other.

U.S. Pat. No. 10,136,925 discloses a spinal cross-connector having an elongated member, a first connector, and a second connector. The first connector and the second connector are configured to receive spinal rods and adaptable to directly attach with pedicle screws. The first connector includes a first collet head, a first clamp and a first locking means. The second connector includes a second collet head, a second clamp and a second locking means. The first locking means is configured to tighten over a first collet head and engage with the first connector. Similarly, the second locking means is configured to tighten over a second collet head and engage with the second connector. The engagement of the first locking means with the first connector and the second locking means with the second connector locks the spinal cross-connector.

U.S. Pat. RE42, 867 discloses an orthopedic device used to fix and stabilize bones to correct anomalies in skeletal structure occurring naturally or by trauma. Bone screws are screwed into bones by application of torque. Clamps are movably attached to the screws. Each clamp includes a compression ring. A connecting rod connects several screws through slots in the clamps. The clamps are tightened to hold the rod and the heads in a pre-selected position by linear movement of the compression rings.

U.S. Pat. No. 10,751,090 discloses a bone anchoring device having a receiving part with a recess for receiving a rod and a flexible head receiving portion for pivotably holding a head of a bone anchoring element, a pressure member configured to exert pressure on the head when the head is held in the head receiving portion, and a clamping ring positionable around the head receiving portion and movable from a first position where the head is pivotable relative to the receiving part, to a second position where the clamping ring exerts a radial force on the head receiving portion to lock the head relative to the receiving part. When the clamping ring is at the first position, the clamping ring abuts the receiving part to restrict upward movement, while a surface of the clamping ring that faces upwards is exposed for engaging an instrument to move the clamping ring to the second position.

U.S. Pat. No. 9,649,135 discloses a low profile orthopedic device using a clamp and compression ring to couple to a bone screw. The clamps are tightened to hold the rod to the bone screws in a preselected position by linear movement of the compression ring.

SUMMARY OF THE DISCLOSURE

The present system provides novel component devices and a method for selectively locking and unlocking a connector to a bone screw using an easily operated, torque-less locking and unlocking instrument specifically designed for use with the novel connector configuration. The spinal fixation system is for use in securing a spinal rod to a vertebra using a bone screw with a lockable connector. The connector is configured to be movably connected to the head of a bone screw wherein a spinal rod can positioned to physically connect a first vertebra to a second vertebra. Once a bone screw has been attached, a connector on the bone screw can be locked in place allowing a spinal rod to be fitted. By locking of the connector to the bone screw, the connector can be used to move the vertebra along the spinal rod. The spinal fixation locking instrument includes a clamp for grasping a groove in the connector and an adjacent collet. The instrument is used to lock the connector to the bone screw by moving the collet from a first position to a second position. The connector can be selectively unlocked from the bone screw for adjustment or removal. Once the spinal rod and bone screw are placed into a desired position, the spinal rod is locked in position in relation to the connector and bone screw by use of a set screw. In one embodiment the bone screw and connector are adjoined at the manufacturing stage. In another embodiment the bone screw and connector are modular allow bone screws of various shanks and sizes to be installed wherein the connector is bottom loading attached during the installation step.

An objective of the invention is to provide a spinal fixation system having a connector that is releasably lockable to a bone screw wherein a locked connector allows movement along a spinal rod for vertebra positioning.

Still another objective of the invention is to provide spinal fixation system having a connector operatively associated with a collet wherein the collet in a first position allows connector movement and the collet in a second position locks connector movement in relation to a bone screw.

Yet still another objective of the invention is to provide a spinal fixation system having minimal components of a bone screw, connector and collet to lower inventory costs, assembly costs, and simplify installation.

Yet another objective of the invention is to provide a spinal fixation system that is preassembled or modular in installation.

Another objective of the invention is to provide a spinal fixation system having a connector with a removable treaded extension allowing ease of attaching a spinal rod and set screw, and removal of the threaded extension to provide a low profile installation.

An advantage of the system is that a surgeon can use the locking instrument to lock each connector to a bone screw. The surgeon can then place a stabilization rod with the connector for alignment purposes. The connector can be unlocked from the bone screw readjust the arrangement of the connector and stabilization rod to better suit the surgical situation. The tool allows the connector to slide along the stabilization rod in the locked position for repositioning of the spine, such as in cased of spine curvature, to obtain superior results.

Another advantage is that the locked position of the connector to the screw provides great flexibility to the surgeon in making any adjustments deemed necessary such as, but not limited to, compression, distraction, and rotation of the entire construct or of individual bodies. After completing the adjustments, the surgeon can then fully lock the stabilization rod by placement of the set screw. The engagement allows the surgeon to quickly mount the stabilizing rod in rapid sequence. Should the surgeon fully remove the connector in a modular system, the instrument may be used to move the collet from the locked position to an unlocked position. In the event of a revision surgery, the unlocking instrument may be used to unlock the connector to allow removal of the screw.

Other objectives and advantages of this invention will become apparent from the following description taken in conjunction with any accompanying drawings wherein are set forth, by way of illustration and example, certain embodiments of this invention. Any drawings contained herein constitute a part of this specification, include exemplary embodiments of the present invention, and illustrate various objects and features thereof.

DETAILED DESCRIPTION OF THE PREFERRED EMBODIMENTS

Detailed embodiments are disclosed herein; however, it is understood that the following description is provided as being exemplary of the invention, which may be embodied in various forms without departing from the scope of the claimed invention. Thus, the specific structural and functional details provided in the description are non-limiting, but serve merely as a basis for the invention defined by the claims provided herewith.

Generally speaking, various embodiments of the present invention provide for a spinal fixation device for orthopedic rod implantation. The invention is not limited to a specific size, diameter, or length and may accommodate a patient of any size, weight, and spinal condition. By way of example, the spinal fixation device employs a pedicle screw that can vary in size, diameter, or length to accommodate the patient's needs. An advantage of the instant invention includes having different sized pedicle screws based on the patient's needs being interchangeable with the same tulip shaped connector, making the instant invention modular and adaptable for different patients.

Referring now to the Figures, illustrated is a preferred embodiment of the spinal fixation device 10. The spinal fixation device 100 includes a bone screw 100, also known as a "pedicle screw", having a first end 102 and a second end 104. Between the first end 102 and the second end 104 defines a shank portion 106 for penetrating securement to a bone. A surgeon will insert the bone screw 100 into the spine of a patient starting from the first end 102 and leading to the second end 104, which is constructed and arranged as a head portion 108.

Further, the bone screw 100 includes at least one continuous thread 110 protruding outwardly from the shank 106 to engage with the bone and provide stabilization of the joint. In a preferred embodiment, the bone screw 100 includes at least one helical thread 110 for penetration and engagement of the bone. The size, shape, and pitch of the continuous thread 110 are not limiting. The pitch of the threads 110 may be consistent or variable. As illustrated in the Figures, continuous threads 110 that are consistent in pitch allow for a standardized size that is suitable as a spinal fusion surgery in most patients. Just as a traditional screw, the threads 110 decrease in diameter closer to the first end 102.

Figure 5A:
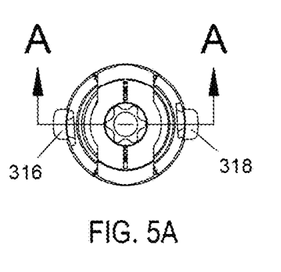
FIG. 5A illustrates a top view of the bone screw with an unlocked connector.
Figure 5B:
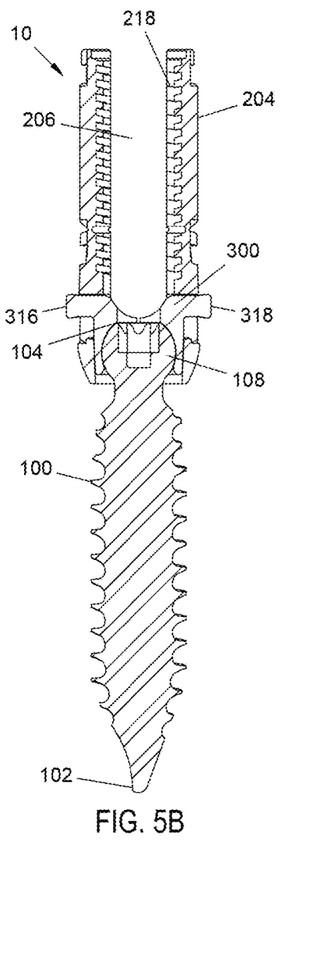
FIG. 5B illustrates a cross-sectional side view taken along line AA of FIG. 5A.
Figure 6A:
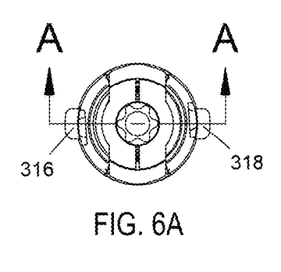
FIG. 6A illustrates a top view of the bone screw with a locked connector.
Figure 6B:
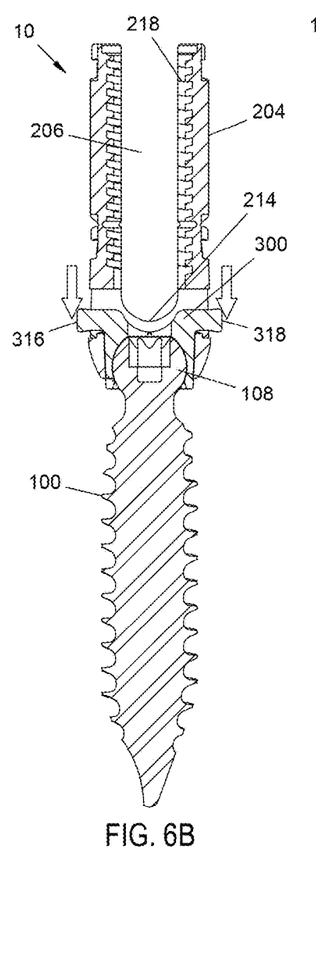
FIG. 6B illustrates a cross-sectional side view taken along line AA of FIG. 6A.

The head portion 108 of the bone screw 100 is shaped to accommodate a tulip shaped connector 200 for securing a stabilizing rod 12 to an anchored bone screw 100. The head portion 108 is preferably at least partially spherical in shape. In the exemplary embodiment shown in FIGS. 5B, 6B, and 7B, the head portion 108 is fully spherical in shape. The size and shape of the head portion 108 is not limiting.

The tulip shaped connector 200 is a modular piece that is seated on the head portion 108 of the bone screw 100. The tulip shaped connector 200 includes an upper section 202 formed from a pair of upright spaced apart arms 204 defining U-shaped openings 206 and a lower section 208 formed from a pair of spaced apart slots 210. In a preferred embodiment, the U-shaped openings 206 are further defined as two diametrically opposed openings on the upright spaced apart arms 204 wherein the stabilizing rod 12 is positioned within the shaped openings 206. The outer surface of the connector 200 has a groove 212 formed perpendicular to the slots 210. The groove 212 acts as a recess that allows a specialized tool to be inserted for the locking and unlocking operation of the spinal fixation device 10. Once the spinal fixation device 10 is in the desired position, a surgeon may remove the tool and fully remove the upright spaced apart arms 204 by breaking reduction tabs 220 along a score 222. The removal of the upright spaced apart arms 204 leaves the spinal fixation device 10 inserted in a patient's spine with a low profile, thereby enhancing the comfort of the implant for the patient since less protrusion of the implant will be present.

Figure 1A:
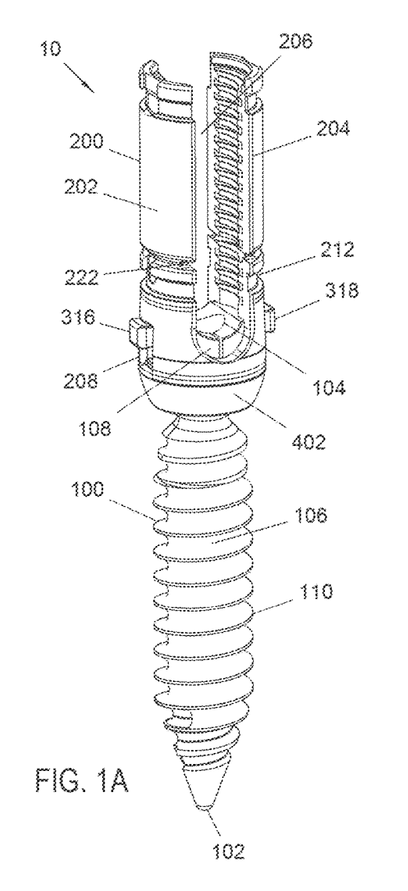
FIG. 1A illustrates a front perspective view of the bone screw with lockable connector.
Figure 1B:
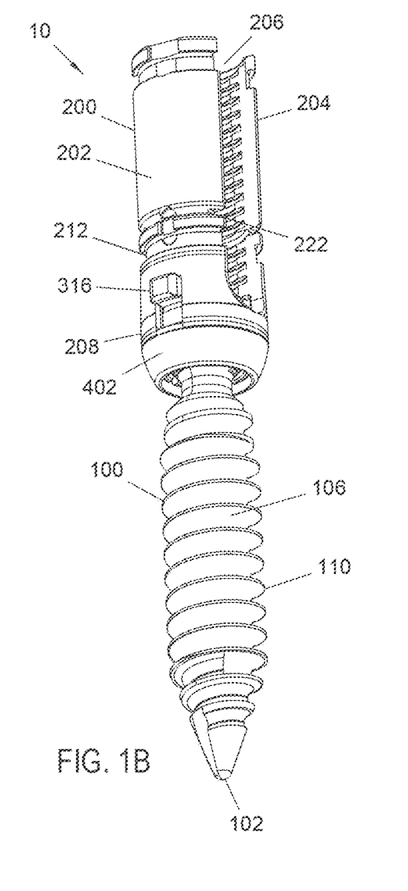
FIG. 1B illustrates a rear perspective view of FIG. 1A.
Figure 2A:
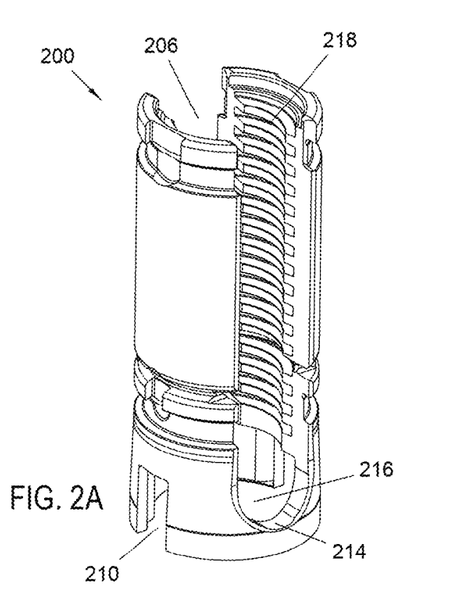
FIG. 2A illustrates a front perspective view of the upper connector.
Figure 2B:
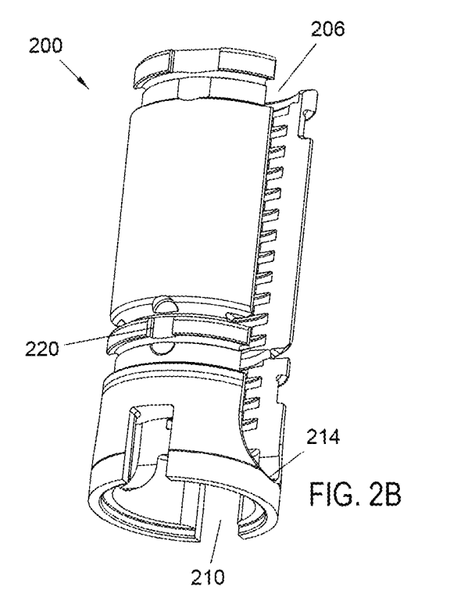
FIG. 2B illustrates a rear perspective view of FIG. 2A.
Figure 3A:
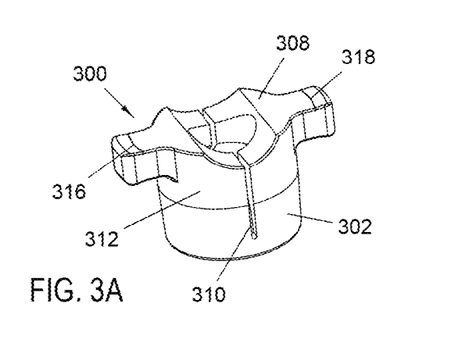
FIG. 3A illustrates an upper perspective view of the collet.
Figure 3B:
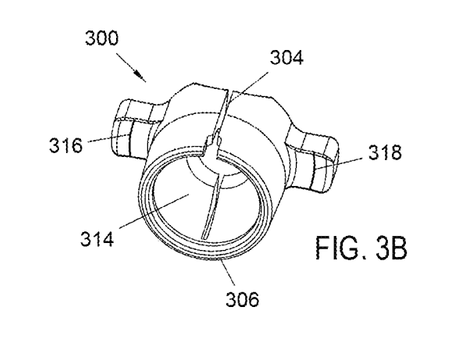
FIG. 3B illustrates a rear perspective view of FIG. 3A.
Figure 4A:
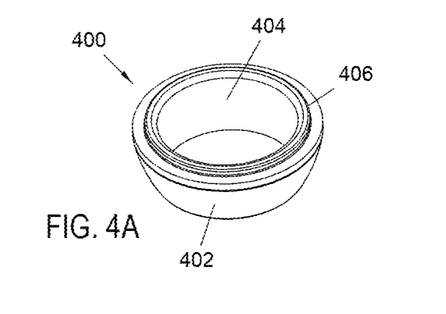
FIG. 4A illustrates an upper perspective view of the upper connector.
Figure 4B:
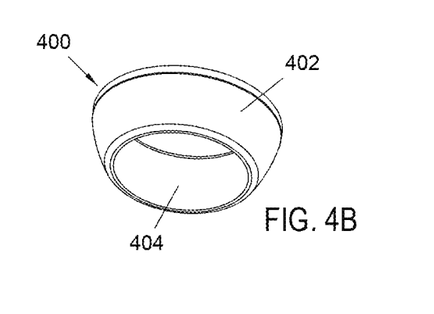
FIG. 4B illustrates a lower perspective view of FIG. 4A.

Additionally, the tulip shaped connector 200 includes an aperture positioned between the upper section 202 and the lower section 208 forming an internal cavity 216. The internal cavity 216 includes a threaded surface 218 that extends along the length of the connector member 200 upper section 202. Located within the upper section 202 and adjacent to the lower section 208 of the tulip shaped connector 200 is a collet member 300, as shown in FIGS. 3A and 3B. The collet member 300 is formed from a substantially conical side wall 302 with a total split 304 extending on one side from a lower edge 306 to an upper edge 308. A partial split 310 is also present on an opposite side of the total split 304 that extends adjacent to the lower edge 306 to the upper edge 308 forming a compression member 312. In a preferred embodiment, the collet 300 is securable to the bone screw 100 by compression when moved along a sloped inner surface 224 of the connector 200.

The total split 304 allows for the side wall 302 to be press fit within upper section 202 of the connector 200. Further, the lower edge 306 forms an upper spherical seating surface 314 for receipt of an upper portion of the bone screw spherical head, or the head portion 108. In an exemplary embodiment, the head portion 108 of the bone screw 100 fits directly into the upper spherical seating surface 314 by being similarly shaped and sized for a proper press fit connection. The head portion 108 frictionally engages the collet 300 for locking the connector 200 to the bone screw 100.

The collet member 300 includes a pair of tabs 316, 318 extending outwardly from the upper edge 308. The tabs 316, 318 fit directly and are slidably disposed within the spaced apart slots 210. This allows for the specialized tool to push medially downwards on the tabs 316, 318 of the collet 300 to lock the bone screw 100 to the tulip shaped connector 200. The slidable engagement also allows the specialized tool to pull the collet 300 laterally to unlock the bone screw 100 from the tulip shaped connector 200 as the tabs 316, 318 move laterally within the spaced apart slots 210. In particular, the spinal fixation device 10 is specifically configured to be capable of releasably connecting to and operationally interacting with the connector 200 and the collet 300 for moving the collet 300 from a first position (I) to a second position (II) within the slots 210, and from the second position (II) to the first position (I) for releasable engagement of the connector 200 to the bone screw 100 to facilitate adjustment or removal of the stabilizing rod 12.

The spinal fixation device 10 includes a connector base 400 having a continuous side wall 402 forming a lower conical seating surface 404 for receipt of the conical side wall 302 of the collet 300. In an exemplary embodiment, the head portion 108 of the bone screw 100 fits directly into the spherical seating surface 314 by being similarly shaped and sized for a proper press fit connection. The connector base 400 itself is secured to the lower section 208 of the connector 200 securing the bone screw 100 and the collet 300 therebetween. In a preferred embodiment, the connector base 400 includes at least one ridge 406 securable to said lower section 208 of the connector 200 by weldment.

Figure 7A:
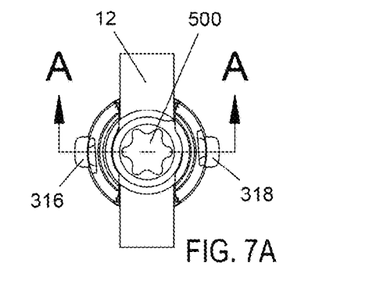
FIG. 7A illustrates a top view of the bone screw with an locked connector clamped to a rod.
Figure 7B:
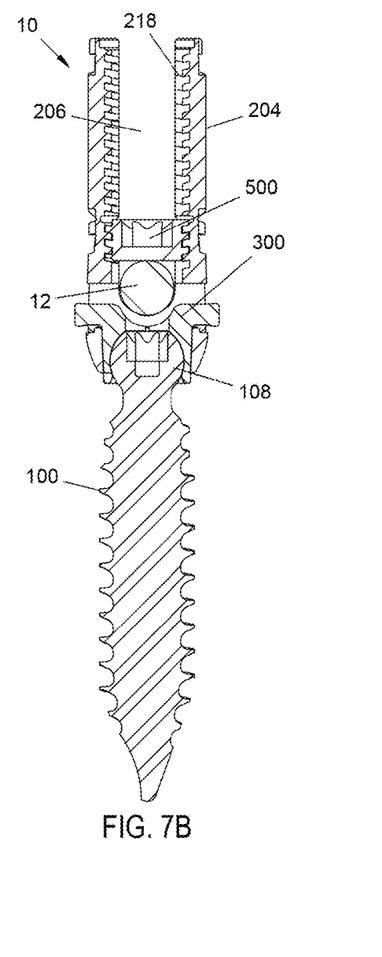
FIG. 7B illustrates a cross-sectional side view taken along line AA of FIG. 7A.
Figure 8A:
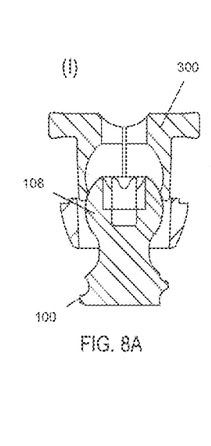
FIG. 8A illustrates a cross-sectional side view of a bone screw inserted within the lower connector shown without the upper connector.
Figure 8B:
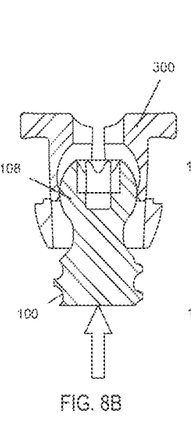
FIG. 8B illustrates a cross-sectional side view of a bone screw inserted within the collet.
Figure 8C:
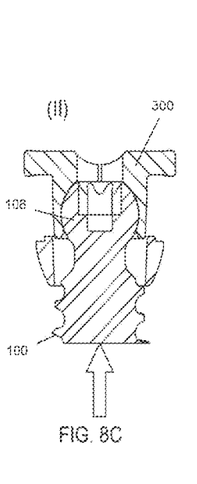
FIG. 8C illustrates a cross-sectional side view of a bone screw un-locked to the collet.
Figure 8D:
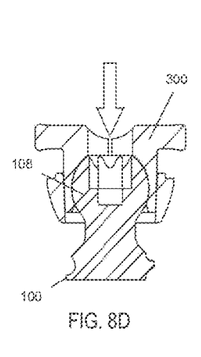
FIG. 8D illustrates a cross-sectional side view of a bone screw locked to the collet.
Figure 9:
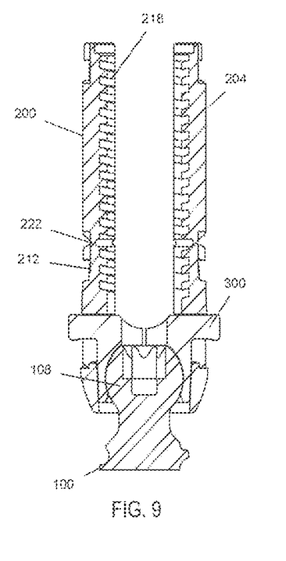
FIG. 9 illustrates a cross-sectional side view with the upper connector welded to the lower connector.

The spinal fixation device 10 can be fully locked by use of a set screw 500, as shown in FIGS. 7A and 7B. The set screw 500 is threadably engageable along the threaded surface 218 of the internal cavity 216 for engaging a stabilizing rod 12 against the collet 300. In an alternative embodiment, the stabilizing rod 12 contacts and engages a rod slot 214 which further allows adequate clearance for the collet 300 to move from a locked position to an un-locked position. The threads on the set screw 500 are configured to prevent splaying of a rod base member 203. In the exemplary embodiment, the set screw 500 is a Torx screw threadably engageable along the threaded surface 218. The set screw 500 may also be a flat head screw or a Phillips screw. The size, shape, pitch, and pattern of the set screw 500 is not limiting.

Figure 10:
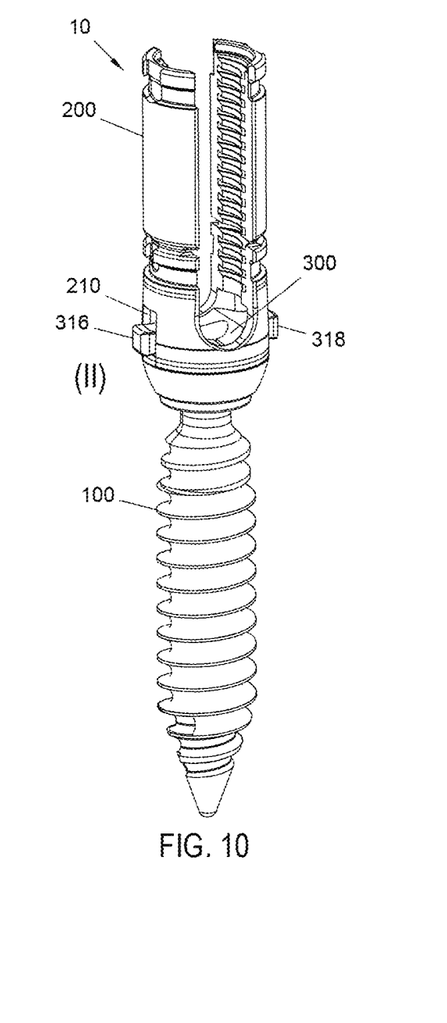
FIG. 10 illustrates a perspective view of the bone screw with the collet in the locked position.
Figure 11:
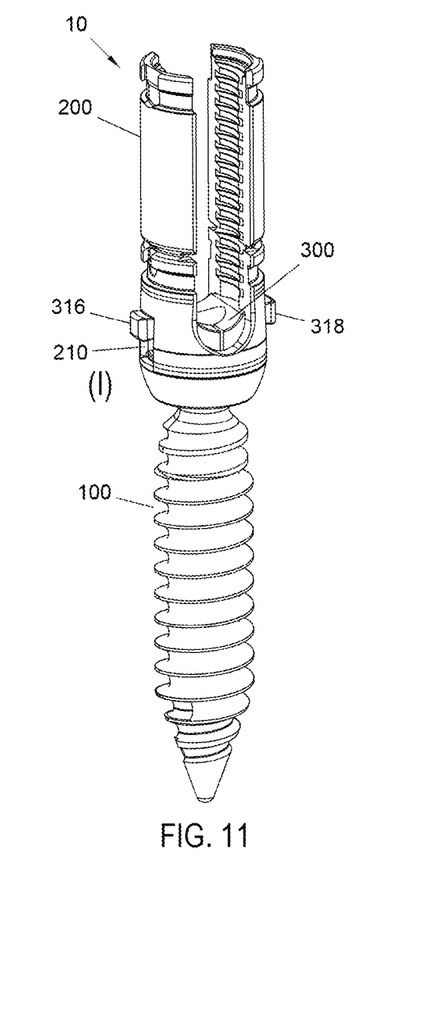
FIG. 11 illustrates a perspective view of the bone screw with connector in an un-locked position.

The assembly procedure of the spinal fixation device 10 is illustrated in FIGS. 8A-8D. Placing the collet 300 in a first position (I) allows movement of the connector 200 in relation to the bone screw 100 and transversely moving the collet 300 to a second position (II) to prepare the spinal fixation device 10 for weldment during the assembly procedure. A stabilizing rod 12 may then be placed in the U-shaped channel 206 and secured thereto by the set screw 500. In an alternative embodiment, moving the collet 300 from a first position (I) to a second position (II) induces compressive forces on the collet 300 to lock the connector 200 in position and placing a rod 12 in the collet 300 with a set screw 500 immobilizes moving between the connector 200 and the rod 12 and the anchored bone screw 100. FIG. 10 shows the collet 300 in a locked position. FIG. 11 shows the collet 300 in an un-locked position.

The term "coupled" is defined as connected, although not necessarily directly, and not necessarily mechanically. The use of the word "a" or "an" when used in conjunction with the term "comprising" in the claims and/or the specification may mean "one," but it is also consistent with the meaning of "one or more" or "at least one." The term "about" means, in general, the stated value plus or minus 5%. The use of the term "or" in the claims is used to mean "and/or" unless explicitly indicated to refer to alternatives only or the alternative are mutually exclusive, although the disclosure supports a definition that refers to only alternatives and "and/or."

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method or device that "comprises," "has," "includes" or "contains" one or more steps or elements, possesses those one or more steps or elements, but is not limited to possessing only those one or more elements. Likewise, a step of a method or an element of a device that "comprises," "has," "includes" or "contains" one more features, possesses those one or more features, but is not limited to possessing only those one or more features. Furthermore, a device or structure that is configured in a certain way is configured in at least that way, but may also be configured in ways that are not listed.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary, and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A spinal fixation device for orthopedic rod implantation, comprising:
    a bone screw having a first end and a second end, said first end constructed and arranged as a shank portion for penetrating securement to a bone, said second end constructed and arranged as a head portion;
    a tulip shaped connector for securing a stabilizing rod to an anchored bone screw, said connector having an upper section formed from a pair of upright spaced apart arms defining U-shaped openings and a lower section formed from a pair of spaced apart vertically disposed slots, said connector having an outer surface groove formed perpendicular to said slots, and an aperture positioned between the upper and lower sections forming an internal cavity, said internal cavity including a threaded surface that extends along the length of the connector member upper section;
    a collet member formed from a substantially cylindrical side wall with a total split extending on one side from a lower edge to an upper edge and a partial split extending on an opposite side extending adjacent to said lower edge to said upper edge forming a compression member, said lower edge forming an upper spherical seating surface for receipt of an upper portion of said bone screw head portion, and a pair of tabs extending outward from the upper edge, said tabs slidably disposed within said spaced apart vertically disposed slots extending through the sidewall of said connector allowing said collet member to be moved by engagement of said tabs for movement of said collet between a first position and a second position for locking of said connector to said bone screw;
    a connector base having a continuous side wall forming a lower spherical seating surface for receipt of a lower portion of said bone screw spherical head, said connector base secured to said lower section of said connector securing said bone screw and said collet therebetween; and
    a set screw threadably engageable along said threaded surface of said internal cavity for engaging a stabilizing rod against said collet;
    wherein placing said collet in said first position allows movement of said connector in relation to said bone screw and transversely moving said collet to said second position locks said connector to said bone screw in a selected position to prevent movement whereby a stabilizing rod placed in said U-shaped channel is secured thereto by said set screw.

2. The spinal fixation device according to claim 1 wherein said U-shaped openings are further defined as two diametrically opposed openings on the upright spaced apart arms wherein the stabilizing rod is positioned within the U-shaped openings.

3. The spinal fixation device according to claim 1 wherein said upright spaced apart arms are scored along an outer surface whereby said arms are removable upon installation to provide a low profile.

4. The spinal fixation device according to claim 1 wherein said connector base includes at least one ridge securable to said lower section of said connector by weldment.

5. The spinal fixation device according to claim 1 wherein said collet is securable to said bone screw by compression when moved along a sloped inner surface of said connector.

6. The spinal fixation device according to claim 1 wherein said bone screw includes at least one helical thread for penetrating and engaging a bone and wherein said head portion is at least partially spherical in shape.

7. A spinal fixation device for orthopedic rod implantation, comprising:
- a bone screw having a first end and a second end, said first end constructed and arranged as a shank portion for penetrating securement to a bone, said second end constructed and arranged as a head portion;
- a tulip shaped connector for securing a stabilizing rod to an anchored bone screw, said connector having an upper section formed from a pair of upright spaced apart arms defining U-shaped openings formed from two diametrically opposed openings on the upright spaced apart arms, and a lower section formed from a pair of spaced apart vertically disposed slots, said connector having an outer surface groove formed perpendicular to said slots, and an aperture positioned between the upper and lower sections forming an internal cavity, said internal cavity including a threaded surface that extends along the length of the connector member upper section;
- a collet member formed from a substantially cylindrical side wall with a total split extending on one side from a lower edge to an upper edge and a partial split extending on an opposite side extending adjacent to said lower edge to said upper edge forming a compression member, said lower edge forming an upper spherical seating surface for receipt of an upper portion of said bone screw head portion, and a pair of tabs extending outward from the upper edge, said tabs slidably disposed within said spaced apart vertically disposed slots extending through the sidewall of said connector allowing said collet member to be moved by engagement of said tabs for movement of said collet between a first position and a second position for locking of said connector to said bone screw;
- a connector base having a continuous side wall forming a lower spherical seating surface for receipt of a lower portion of said bone screw spherical head, said connector base secured to said lower section of said connector securing said bone screw and said collet therebetween, said connector base includes at least one ridge securable to said lower section of said connector by weldment; and
- a set screw threadably engageable along said threaded surface of said internal cavity for engaging a stabilizing rod against said collet;
- wherein placing said collet in said first position allows movement of said connector in relation to said bone screw and transversely moving said collet to said second position locks said connector to said bone screw in a selected position to prevent movement whereby a stabilizing rod placed in said U-shaped channel is secured thereto by said set screw.

8. The spinal fixation device according to claim 7 wherein said upright spaced apart arms are scored along an outer surface whereby said arms are removable upon installation to provide a low profile.

9. The spinal fixation device according to claim 7 wherein said collet is securable to said bone screw by compression when moved along a sloped inner surface of said connector.

10. The spinal fixation device according to claim 7 wherein said bone screw includes at least one helical thread for penetrating and engaging a bone and wherein said head portion is at least partially spherical in shape.

11. A spinal fixation kit for orthopedic rod implantation, comprising:
- at least one bone screw having a first end and a second end, said first end constructed and arranged as a shank portion for penetrating securement to a bone, said second end constructed and arranged as a head portion;
- a connector for securing a stabilizing rod to an anchored bone screw, said connector having an upper section formed from a pair of upright spaced apart arms defining U-shaped openings and a lower section formed from a pair of spaced apart vertically disposed slots, said connector having an outer surface groove formed perpendicular to said slots, and an aperture positioned between the upper and lower sections forming an internal cavity, said internal cavity including a threaded surface that extends along the length of the connector member upper section;
- a collet member formed from a substantially cylindrical side wall with a total split extending on one side from a lower edge to an upper edge and a partial split extending on an opposite side extending adjacent to said lower edge to said upper edge forming a compression member, said lower edge forming an upper spherical seating surface for receipt of an upper portion of said bone screw head portion, and a pair of tabs extending outward from the upper edge, said tabs slidably disposed within said spaced apart vertically disposed slots extending through the sidewall of said connector allowing said collet member to be moved by engagement of said tabs for movement of said collet between a first position and a second position for locking of said connector to said bone screw;
- a connector base having a continuous side wall forming a lower spherical seating surface for receipt of a lower portion of said bone screw spherical head, said connector base secured to said lower section of said connector securing said bone screw and said collet therebetween; and
- a set screw threadably engageable along said threaded surface of said internal cavity for engaging a stabilizing rod against said collet;
- wherein moving said collet from said first position to said second position induces compressive forces on said collet to lock said connector in position and placing a rod in said connector with a set screw immobilizes moving between said connector and said rod and said anchored bone screw.

* * * * *